United States Patent
Lee et al.

(10) Patent No.: US 6,359,153 B1
(45) Date of Patent: Mar. 19, 2002

(54) PHOTORESIST MONOMERS AND PREPARATION THEREOF

(75) Inventors: Geun Su Lee; Chang Il Choi; Hyeong Soo Kim; Jin Soo Kim; Jae Chang Jung; Min Ho Jung; Ki Ho Baik, all of Kyoungki-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 0 days.

(21) Appl. No.: 09/428,171

(22) Filed: Oct. 27, 1999

(30) Foreign Application Priority Data

Oct. 28, 1998 (KR) .............................. 98/45599
Nov. 16, 1998 (KR) .............................. 98-49022

(51) Int. Cl.$^7$ ..................... C07D 307/00; C07C 41/09; C07C 41/50; C07C 43/04; C07C 43/30
(52) U.S. Cl. ..................... 549/463; 568/664; 568/667; 568/670; 430/270.1
(58) Field of Search ................ 549/463; 568/664, 568/667, 670; 430/270.1

(56) References Cited

U.S. PATENT DOCUMENTS 5,254,638 A * 10/1993 Novak et al.
5,990,177 A * 11/1999 Brown

FOREIGN PATENT DOCUMENTS

WO          WO 99/14256          3/1999

OTHER PUBLICATIONS

Novak et al., J. Am. Chem. Soc. (1988), vol. 110 No. 3, pp. 960–961.*

\* cited by examiner

Primary Examiner—T. A. Solola
(74) Attorney, Agent, or Firm—Townsend and Townsend and Crew LLP

(57) ABSTRACT

The present invention relates to monomers for preparing photoresist polymer resins which can be used in a photolithography process employing a deep ultraviolet light source, and the preparation of the same. Preferred monomers are represented by following Chemical Formula 1:

<Chemical Formula 1>

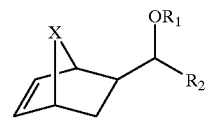

wherein, X represents $CH_2$, $CH_2CH_2$, or oxygen;

$R_1$ represents hydrogen, $C_1$–$C_5$ alkyl, or R'OH;

$R_2$ represents hydrogen; —OH, $C_1$–$C_5$ alkoxy, or —OR'—OH;

R' represents:

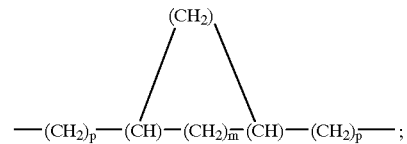

and, m is an integer from 1–5, n is 1 or 2 and p is 0 or 1.

8 Claims, No Drawings

PHOTORESIST MONOMERS AND PREPARATION THEREOF

FIELD OF THE INVENTION

The present invention relates to novel monomers used for preparing a photoresist copolymer, and a process for preparing the same. More specifically, it relates to monomers useful for forming photoresist polymer resins which have suitable properties for lithography processes using a light source employing deep ultraviolet region radiation, and a process for preparing the same.

BACKGROUND OF THE INVENTION

In general, excellent etching resistance, heat resistance, adhesiveness and resolution are requisites for a photoresist resin. However, most of the conventional ArF photoresists have insufficient etching resistance, and cannot fully satisfy those properties. For example, the photoresist polymer resins comprising an alicyclic compound as a monomer have excellent etching resistance and resolution, but the absorbance of the photoresist at the wavelength of ArF light is so high that a pattern of high integrity and high resolution could not be obtained.

SUMMARY OF THE INVENTION

The object of the present invention is to solve the problems described above, and to provide novel photoresist monomers which impart excellent etching resistance and adhesiveness to photoresist polymers so as to be suitable for lithography processes using a deep ultraviolet light source.

Through intensive studies and research, the present inventors have developed monomers that can overcome the problems associated with developing a high-performance photoresist. As a result, they have found that when a compound having one or more hydroxyl groups or alkoxy groups, such as a compound of Chemical Formula 1 below, is used as a monomer for preparing a photoresist copolymer, adhesiveness of the photoresist to a silicon wafer is considerably enhanced, and a resist having excellent resolution and etching resistance can be developed.

The present invention provides a novel photoresist monomer represented by following Chemical Formula 1:

<Chemical Formula 1>

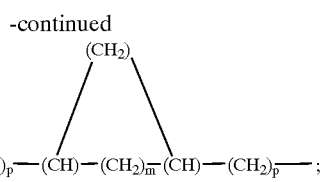

wherein, X represents $CH_2$, $CH_2CH_2$, or oxygen;

$R_1$ represents hydrogen, $C_1$–$C_5$ alkyl, or R'OH;

$R_2$ represents hydrogen; —OH, $C_1$–$C_5$ alkoxy, or —OR'—OH;

R' represents:

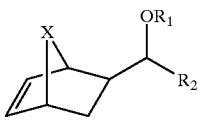

-continued

and m is an integer from 1–5, n is 1 or 2 and p is 0 or 1.

Preferably R'OH is selected from the group consisting of the following groups (2)–(9):

(2)
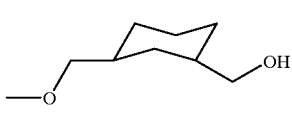

(3)
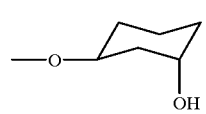

(4)
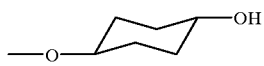

(5)
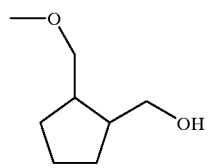

(6)
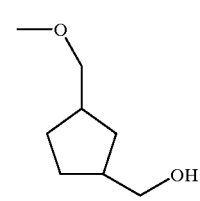

(7)

(8)
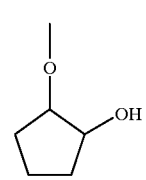

(9)
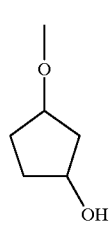

The compounds of Chemical Formula 1 are synthesized by reacting (i) a compound represented by Chemical Formula 2 below with (ii) an alkyl compound having one or more hydroxyl group(s), in the presence of a base or acid catalyst in an organic solvent.

<Chemical Formula 2>

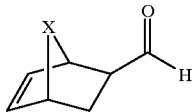

wherein, X represents $CH_2$, $CH_2CH_2$, or oxygen.

Examples of suitable alkyl compounds having hydroxyl substituent(s) include methanol, ethanol, propanol, ethylene glycol, trimethylene glycol, 1,4-butanediol, 1,5-pentanediol, diethylene glycol, triethylene glycol, 1,4-cyclohexanedimethanol, 1,3-cyclohexanedimethanol, 1,3-cyclohexanediol, 1,4-cyclohexanediol, 1,3-cyclopentanedimethanol, 1,2-cyclopentanedimethanol, 1,3-cyclopentanediol, and 1,2-cyclopentanediol.

As the acid catalyst, sulfuric acid, hydrochloric acid, nitric acid or acetic acid may be used. As the base catalyst, sodium hydride (NaH), potassium hydride (KH), calcium hydride ($CaH_2$) or lithium diisopropyl amide (LDA) may be used. As the reaction solvent, tetrahydrofuran (THF), dimethylformamide, dimethylsulfoxide, dioxane, benzene, toluene, or xylene may be used.

The compounds according to the present invention can be effectively used as a monomer for synthesizing a photoresist resin for electron-beam, ArF, KrF, EUV, VUV (Vacuum Ultra Violet) and X-ray radiation, which can be employed in micro lithography processes to form high-integrity patterns of 0.15 μm or less (DRAM of 1G or more). Since the monomers according to the present invention comprise one or more hydroxyl group or alkoxy group, adhesiveness can be considerably enhanced when they are employed in the synthesis of a photoresist resin, and a resist having excellent resolution and etching resistance can be developed therefrom.

Photoresist copolymer resins may be prepared by polymerizing a monomer of Chemical Formula 1 with at least one other monomer, for example with one or more alicyclic olefin monomers. Polymerization may be carried out using conventional bulk polymerization or solution polymerization processes.

DETAILED DESCRIPTION

The invention is described in more detail by referring to the examples below, but it should be noted that the present invention is not restricted to the examples.

EXAMPLE 1

Synthesis of 5-norbornene-2-(1-methoxy)methanol 5-norbornene-2-carboxaldehyde (0.1 mole), sulfuric acid (0.3 ml) and methanol (500 ml) were reacted at room temperature for 10 hours. After the reaction was completed, methanol was distilled off by using a rotary evaporator. To the residual solution, 200 ml of water and 300 ml of ethyl acetate were added, and the mixture was extracted. The organic layer was washed with water (300 ml) once more, dried over anhydrous magnesium sulfate and filtered. The filtrate was evaporated by using a rotary evaporator. The residue was distilled under high vacuum to obtain the compound of Chemical Formula 3 as a colorless and clear liquid (13 g/yield: 93%).

<Chemical Formula 3>

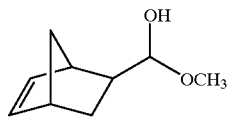

EXAMPLE 2

Synthesis of 5-norbornene-2-(1-ethoxy)methanol 5-norbornene-2-carboxaldehyde (0.1 mole), sulfuric acid (0.3 ml) and ethanol (500 ml) were reacted at room temperature for 10 hours. After the reaction was completed, the reaction mixture was worked up as in the procedure of Example 1, to obtain the compound of Chemical Formula 4 as a colorless and clear liquid (15 g/yield: 91%).

<Chemical Formula 4>

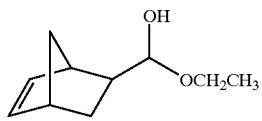

EXAMPLE 3

Synthesis of 5-norbornene-2-(1-propyloxy)methanol 5-norbornene-2-carboxaldehyde (0.1 mole), sulfuric acid (0.3 ml) and propanol (500 ml) were reacted at room temperature for 12 hours. After the reaction was completed, the reaction mixture was worked up as in the procedure of Example 1, to obtain the compound of Chemical Formula 5 as a colorless and clear liquid (17 g/yield: 91%).

<Chemical Formula 5>

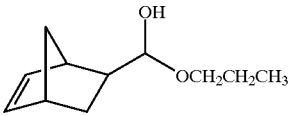

EXAMPLE 4

Synthesis of 5-norbornene-2-hydroxyethoxymethanol 5-norbornene-2-carboxaldehyde (0.1 mole), sulfuric acid (0.3 ml) and ethylene glycol (100 ml) were reacted at room temperature for 10 hours. After the reaction was completed, the reaction mixture was worked up as in the procedure of Example 1, to obtain the compound of Chemical Formula 6 as a colorless and clear liquid (16 g/yield: 89%).

<Chemical Formula 6>

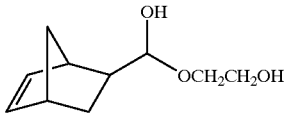

EXAMPLE 5

Synthesis of 5-norbornene-2-hydroxypropyloxy methanol 5-norbornene-2-carboxaldehyde (0.1 mole), sulfuric acid (0.3 ml) and trimethylene glycol (100 ml) were reacted at room temperature for 12 hours. After the reaction was completed, the reaction mixture was worked up as in the procedure of Example 1, to obtain the compound of Chemical Formula 7 as a colorless and clear liquid (17 g/yield: 85%).

<Chemical Formula 7>

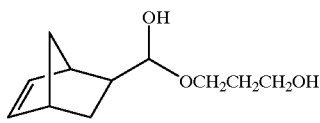

EXAMPLE 6

Synthesis of 5-norbornene-2-hydroxybutyloxy methanol 5-norbornene-2-carboxaldehyde (0.1 mole), sulfuric acid (0.3 ml) and 1,4-butanediol (100 ml) were reacted at room temperature for 12 hours. After the reaction was completed, the reaction mixture was worked up as in the procedure of Example 1, to obtain the compound of Chemical Formula 8 as a colorless and clear liquid (18 g/yield: 86%).

<Chemical Formula 8>

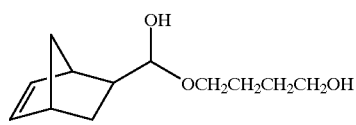

EXAMPLE 7

Synthesis of 5-norbornene-2-hydropentyloxy methanol 5-norbornene-2-carboxaldehyde (0.1 mole), sulfuric acid (0.3 ml) and 1,5-pentanediol (100 ml) were reacted at room temperature for 12 hours. After the reaction was completed, the reaction mixture was worked up as in the procedure of Example 1, to obtain the compound of Chemical Formula 9 as a colorless and clear liquid (19 g/yield: 83%).

<Chemical Formula 9>

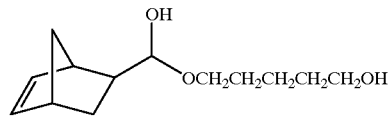

EXAMPLE 8

Synthesis of 5-norbornene-2-hydroxyethoxyethoxy methanol 5-norbornene-2-carboxaldehyde (0.1 mole), sulfuric acid (0.3 ml) and diethylene glycol (100 ml) were reacted at 80° C. for 12 hours. After the reaction was completed, the reaction mixture was worked up as in the procedure of Example 1, to obtain the compound of Chemical Formula 10 as a colorless and clear liquid (20 g/yield: 85%).

<Chemical Formula 10>

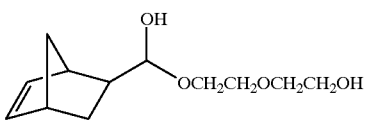

EXAMPLE 9

Synthesis of 5-norbornene-2-hydroxyethoxy methanol 5-norbornene-2-carboxaldehyde (0.1 mole), sulfuric acid (0.3 ml) and triethylene glycol (100 ml) were reacted at room temperature for 12 hours. After the reaction was completed, the reaction mixture was worked up as in the procedure of Example 2, to obtain the compound of Chemical Formula 11 as a colorless and clear liquid (22 g/yield: 79%).

<Chemical Formula 11>

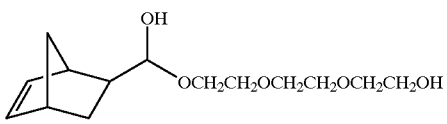

EXAMPLE 10

Synthesis of 5-norbornene-2-(4-hydroxymethyl) cyclohexylmethoxymethanol

To a solution of sodium hydride (0.1 mole) in 100 ml of 1,4-cyclohexanedimethanol, 5-norbornene-2-carboxaldehyde (0.1 mole) was slowly added at room temperature, and the mixture was reacted at the same temperature for 10 hours. To the solution, water (300 ml) and ethyl acetate (500 ml) were added, and the resultant mixture was extracted. After washing with water (300 ml) once more, the organic layer was dried over anhydrous magnesium sulfate, filtered and evaporated by a rotary evaporator. The residue was distilled under high vacuum, to obtain the compound of Chemical Formula 12 as a colorless and clear liquid (25 g/yield: 93%).

<Chemical Formula 12>

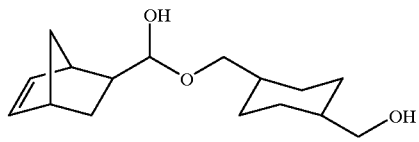

EXAMPLE 11

Synthesis of 5-norbornene-2-(3-hydroxymethyl) cyclohexylmethoxymethanol

To a solution of sodium hydride (0.1 mole) in 100 ml of 1,3-cyclohexanedimethanol, 5-norbornene-2-carboxaldehyde (0.1 mole) was slowly added at room temperature, and the mixture was reacted at the same temperature for 10 hours. To the solution, water (300 ml)

and ethyl acetate (500 ml) were added, and the resultant mixture was extracted. After washing with water (300 ml) once more, the organic layer was dried over anhydrous magnesium sulfate, filtered and evaporated by a rotary evaporator. The residue was distilled under high vacuum, to obtain the compound of Chemical Formula 13 as a colorless and clear liquid (24 g/yield: 91%).

<Chemical Formula 13>

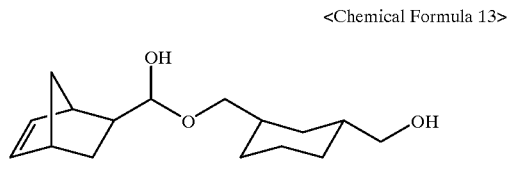

EXAMPLE 12

Synthesis of 5-norbornene-2-(3-hydroxy) cyclohexyloxy methanol

To a solution of sodium hydride (0.1 mole) in 100 ml of 1,3-cyclohexanediol, 5-norbornene-2-carboxaldehyde (0.1 mole) was slowly added at room temperature, and the mixture was reacted at the same temperature for 10 hours. To the solution, water (300 ml) and ethyl acetate (500 ml) were added, and the resultant mixture was extracted. After washing with water (300 ml) once more, the organic layer was dried over anhydrous magnesium sulfate, filtered and evaporated by a rotary evaporator. The residue was distilled under high vacuum, to obtain the compound of Chemical Formula 14 as a colorless and clear liquid (21 g/yield: 88)%.

<Chemical Formula 14>

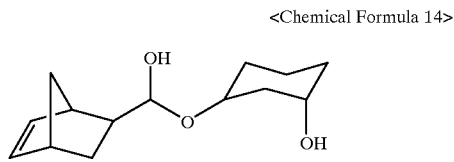

EXAMPLE 13

Synthesis of 5-norbornene-2-(4-hydroxy) cyclohexyloxy methanol

To a solution of sodium hydride (0.1 mole) in 100 ml of 1,4-cyclohexanediol, 5-norbornene-2-carboxaldehyde (0.1 mole) was slowly added at room temperature, and the mixture was reacted at the same temperature for 10 hours. To the solution, water (300 ml) and ethyl acetate (500 ml) were added, and the resultant mixture was extracted. After washing with water (300 ml) once more, the organic layer was dried over anhydrous magnesium sulfate, filtered and evaporated by a rotary evaporator. The residue was distilled under high vacuum, to obtain the compound of Chemical Formula 15 as a colorless and clear liquid (22 g/yield: 92%).

<Chemical Formula 15>

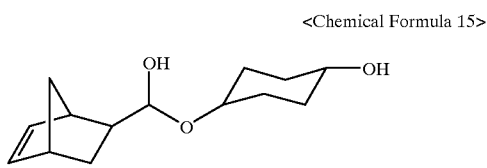

EXAMPLE 14

Synthesis of 5-norbornene-2-(3-hydroxymethyl) cyclopentylnethoxy methanol

To a solution of sodium hydride (0.1 mole) in 100 ml of 1,3-cyclopentanedimethanol, 5-norbornene-2-carboxaldehyde (0.1 mole) was slowly added at room temperature, and the mixture was reacted at the same temperature for 10 hours. After the reaction was completed, the reaction mixture was worked up as in the procedure of Example 11, to obtain the compound of Chemical Formula 16 as a colorless and clear liquid (23 g/yield: 90%).

<Chemical Formula 16>

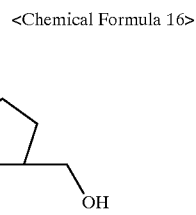

EXAMPLE 15

Synthesis of 5-norbornene-2-(2-hydroxymethyl) cyclopentylmethoxymethanol

To a solution of sodium hydride (0.1 mole) in 100 ml of 1,2-cyclopentanedimethanol, 5-norbornene-2-carboxaldehyde (0.1 mole) was slowly added at room temperature, and the mixture was reacted at the same temperature for 10 hours. After the reaction was completed, the reaction mixture was worked up as in the procedure of Example 11, to obtain the compound of Chemical Formula 17 as a colorless and clear liquid (23 g/yield: 90%).

<Chemical Formula 17>

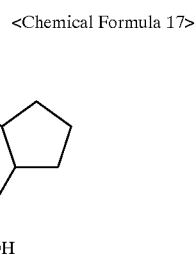

EXAMPLE 16

Synthesis of 5-norbornene-2-(3-hydroxy) cyclopentyloxymethanol

To a solution of sodium hydride (0.1 mole) in 100 ml of 1,3-cyclopentanediol, 5-norbornene-2-carboxaldehyde (0.1 mole) was slowly added at room temperature, and the mixture was reacted at the same temperature for 10 hours. After the reaction was completed, the reaction mixture was worked up as in the procedure of Example 11, to obtain the compound of Chemical Formula 18 as a colorless and clear liquid (20 g/yield: 87%).

<Chemical Formula 18>

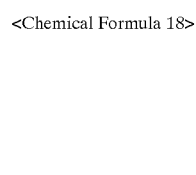

EXAMPLE 17

Synthesis of 5-norbornene-2-(2-hydroxy) cyclopentyloxymethanol

To a solution of sodium hydride (0.1 mole) in 100 ml of 1,2-cyclopentanediol, 5-norbornene-2-carboxaldehyde (0.1 mole) was slowly added at room temperature, and the mixture was reacted at the same temperature for 10 hours. After the reaction was completed, the reaction mixture was worked up as in the procedure of Example 11, to obtain the compound of Chemical Formula 19 as a colorless and clear liquid (20.4 g/yield: 85%).

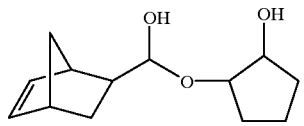

<Chemical Formula 19>

EXAMPLE 18

Synthesis of oxabicyclo[2.2.1]-hept-5-ene-2-methanol

Oxabicyclo[2.2.1]hept-5-ene-2-carboxaldehyde (0.1 mole) was dissolved in 300 ml of ethyl alcohol, and 0.1 mole of $NaBH_4$ was slowly added thereto at room temperature. After stirring for 1 hour, the reaction mixture was heated under reflux for 10 hours. After the reaction was completed, ethyl alcohol was distilled off. Acetone (200 ml) was added thereto, and the mixture was heated under reflux for 1 hour to remove excess $NaBH_4$. After distilling off acetone, 100 ml of 10% hydrochloric acid was added to the residue, and the mixture was stirred for 10 minutes. Water (200 ml) and ethyl acetate (300 ml) were added thereto, and the mixture was extracted. After washing with water (300 ml) once more, the organic layer was dried over anhydrous magnesium sulfate and filtered. After evaporation in vacuo by using a rotary evaporator, the residue was distilled under high vacuum, to obtain the compound of Chemical Formula 20 as a colorless and clear liquid (11 g/yield: 87%).

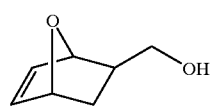

<Chemical Formula 20>

EXAMPLE 19

Synthesis of oxabicyclo[2.2.1]-hept-5-ene-2-(1-methoxy)methanol

Oxabicyclo[2.2.1]hept-5-ene-2-carboxaldehyde (0.1 mole), sulfuric acid (0.3 ml) and methanol (500 ml) were reacted under reflux for 10 hours. Then, methanol was distilled off by using a rotary evaporator. To the reaction mixture, water (200 ml) and ethyl acetate (300 ml) were added, and the mixture was extracted. After washing with water (300 ml) once more, the organic layer was dried over anhydrous magnesium sulfate and filtered. After evaporation in vacuo by using a rotary evaporator, the residue was distilled under high vacuum, to obtain the compound of Chemical Formula 21 as a colorless and clear liquid (13 g/yield: 93%).

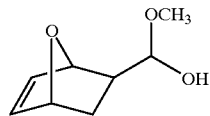

<Chemical Formula 21>

EXAMPLE 20

Synthesis of oxabicyclo[2.2.1]-hept-5-ene-2-(1-ethoxy)methanol

Oxabicyclo[2.2.1]hept-5-ene-2-carboxaldehyde (0.1 mole) sulfuric acid (0.3 ml) and ethanol (500 ml) were reacted under reflux for 10 hours. After the reaction was completed, the procedure of Example 19 was repeated to obtain the compound of Chemical Formula 22 as a colorless and clear liquid (13 g/yield: 91%)

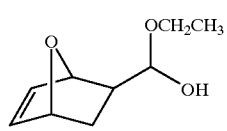

<Chemical Formula 22>

EXAMPLE 21

Synthesis of oxabicyclo[2.2.1]-hept-5-ene-2-(1-propoxy)methanol

Oxabicyclo[2.2.1]hept-5-ene-2-carboxaldehyde (0.1 mole) sulfuric acid (0.3 ml) and propanol (500 ml) were reacted under reflux for 10 hours. After the reaction was completed, the procedure of Example 19 was repeated to obtain the compound of Chemical Formula 23 as a colorless and clear liquid (17 g/yield: 91%)

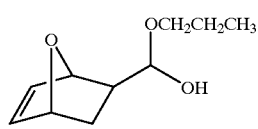

<Chemical Formula 23>

EXAMPLE 22

Synthesis of oxabicyclo2.2.1]hept-5-ene-2-(2-hydroxyethoxy)methanol

Oxabicyclo[2.2.1]hept-5-ene-2-carboxaldehyde (0.1 mole), sulfuric acid (0.3 ml) and ethylene glycol (100 ml) were reacted under reflux at 80° C. After the reaction was completed, the procedure of Example 19 was repeated to obtain the compound of Chemical Formula 24 as a colorless and clear liquid (16 g/yield: 89%)

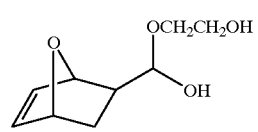

<Chemical Formula 24>

EXAMPLE 23

Synthesis of oxabicyclo[2.2.1]hept-5-ene-2-(3-hydroxypropoxy)methanol

Oxabicyclo[2.2.1]hept-5-ene-2-carboxaldehyde (0.1 mole), sulfuric acid (0.3 ml) and trimethylene glycol (100 ml) were reacted under reflux for 12 hours at 80° C. After the reaction was completed, the procedure of Example 19 was repeated to obtain the compound of Chemical Formula 25 as a colorless and clear liquid (17 g/yield: 85%).

<Chemical Formula 19>

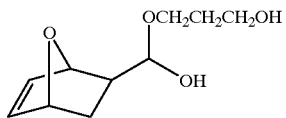

EXAMPLE 24

Synthesis of oxabicyclo[2.2.1]hept-5-ene-2-(4-hydroxybutoxy methanol

Oxabicyclo[2.2.1]hept-5-ene-2-carboxaldehyde (0.1 mole), sulfuric acid (0.3 ml) and 1,4-butanediol (100 ml) were reacted under reflux for 12 hours at 80° C. After the reaction was completed, the procedure of Example 19 was repeated to obtain the compound of Chemical Formula 26 as a colorless and clear liquid (18 g/yield: 86%)

<Chemical Formula 26>

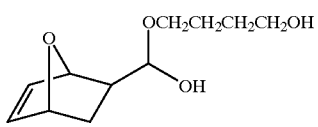

EXAMPLE 25

Synthesis of oxabicyclo[2.2.1]hept-5-ene-2-(5-hydroxypentoxy)methanol

Oxabicyclo[2.2.1]hept-5-ene-2-carboxaldehyde (0.1 mole), sulfuric acid (0.3 ml) and 1,5-pentanediol (100 ml) were reacted under reflux for 12 hours at 80° C. After the reaction was completed, the procedure of Example 19 was repeated to obtain the compound of Chemical Formula 27 as a colorless and clear liquid (19 g/yield: 83%)

<Chemical Formula 27>

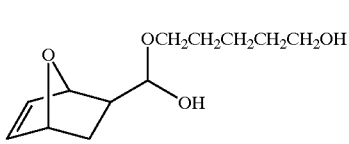

EXAMPLE 26

Synthesis of oxabicyclo[2.2.1]hept-5-ene-2-[2-(2'-hydroxyethoxy)ethoxy]methanol

Oxabicyclo[2.2.1]hept-5-ene-2-carboxaldehyde (0.1 mole), sulfuric acid (0.3 ml) and diethylene glycol (100 ml) were reacted under reflux for 12 hours at 80° C. After the reaction was completed, the procedure of Example 19 was repeated to obtain the compound of Chemical Formula 28 as a colorless and clear liquid (20 g/yield: 85%)

<Chemical Formula 28>

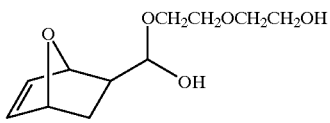

EXAMPLE 27

Synthesis of oxabicyclo[2.2.1]hept-5-ene-2-{2-[2-(2'2''-hydroxyethoxy)ethoxy]ethoxy}methanol Oxabicyclo[2.2.1]hept-5-ene-2-carboxaldehyde (0.1 mole), sulfuric acid (0.3 ml) and triethylene glycol (100 ml) were reacted under reflux for 12 hours at 80° C. After the reaction was completed, the procedure of Example 19 was repeated to obtain the compound of Chemical Formula 29 as a colorless and clear liquid (22 g/yield: 85%)

<Chemical Formula 29>

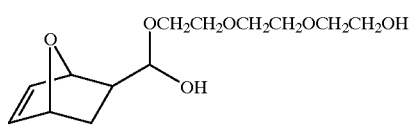

EXAMPLE 28

Synthesis of oxabicyclo[2.2.1]hept-5-ene-2-[(4-hydroxymethyl cyclohexyl)methoxy]methanol To a solution of sodium hydride (0.1 mole) in 100 ml of 1,4-cyclohexanedimethanol, oxabicyclo[2.2.1]-hept-5-ene-2-carboxaldehyde (0.1 mole) was slowly added at room temperature, and the mixture was reacted at the same temperature for 10 hours. To the solution, water (200 ml) and ethyl acetate (500 ml) was added, and the resultant mixture was extracted. After washing with water (300 ml) once more, the organic layer was dried over anhydrous magnesium sulfate, filtered and evaporated in vacuo by using a rotary evaporator. The residue was distilled under high vacuum, to obtain the compound of Chemical Formula 30 as a colorless and clear liquid (25 g/yield: 93%).

<Chemical Formula 30>

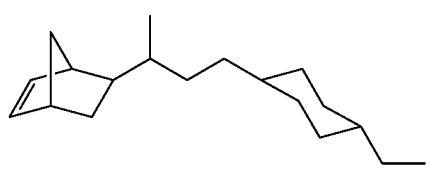

EXAMPLE 29

Synthesis of oxabicyclo[2.2.1]hept-5-ene-2-[(3-hydroxymethyl cyclohexyl)methoxylmethanol To a solution of sodium hydride (0.1 mole) in 100 ml of 1,3-cyclohexanedimethanol, oxabicyclo[2.2.1]-hept-5-ene-2-carboxaldehyde (0.1 mole) was slowly added at room temperature, and the mixture was reacted at the same temperature for 10 hours. To the solution, water (200 ml) and ethyl acetate (500 ml) were added, and the resultant mixture was extracted. After washing with water (300 ml) once more, the organic layer was dried over anhydrous magnesium sulfate, filtered and evaporated in vacuo by using a rotary evaporator. The residue was distilled under high vacuum, to obtain the compound of Chemical Formula 31 as a colorless and clear liquid (24 g/yield: 91%).

<Chemical Formula 31>

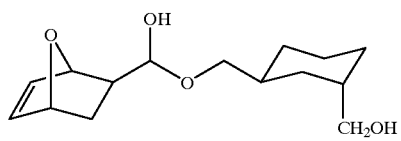

EXAMPLE 30

Synthesis of oxabicyclo[2.2.1]hept-5-ene-2-(3-hydroxycyclohexyloxy)methanol

To a solution of sodium hydride (0.1 mole) in 100 ml of 1,3-cyclohexanediol, oxabicyclo[2.2.1]-hept-5-ene-2-carboxaldehyde (0.1 mole) was slowly added at room temperature, and the mixture was reacted at the same temperature for 10 hours. To the solution, water (200 ml) and ethyl acetate (500 ml) were added, and the resultant mixture was extracted. After washing with water (300 ml) once more, the organic layer was dried over anhydrous magnesium sulfate, filtered and evaporated in vacuo by using a rotary evaporator. The residue was distilled under high vacuum, to obtain the compound of Chemical Formula 32 as a colorless and clear liquid (yield: 88%).

<Chemical Formula 32>

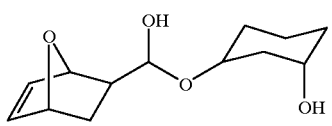

EXAMPLE 31

Synthesis of oxabicyclo2.2.1]hept-5-ene-2-(4-hydroxycyclohexyloxy)methanol

To a solution of sodium hydride (0.1 mole) in 100 ml of 1,4-cyclohexanediol, oxabicyclo[2.2.1]-hept-5-ene-2-carboxaldehyde (0.1 mole) was slowly added at room temperature, and the mixture was reacted at the same temperature for 10 hours. To the solution, water (200 ml) and ethyl acetate (500 ml) were added, and the resultant mixture was extracted. After washing with water (300 ml) once more, the organic layer was dried over anhydrous magnesium sulfate, filtered and evaporated in vacuo by using a rotary evaporator. The residue was distilled under high vacuum, to obtain the compound of Chemical Formula 33 as a colorless and clear liquid (22 g/yield: 92%).

<Chemical Formula 33>

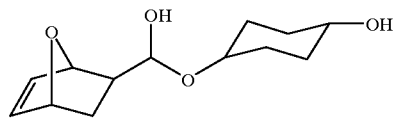

EXAMPLE 32

Synthesis of oxabicyclo[2.2.1]hept-5-ene-2-[(3-hydroxymethyl cyclopentyl)methoxy]methanol To a solution of sodium hydride (0.1 mole) in 100 ml of 1,3-cyclopentanedimethanol, oxabicyclo[2.2.1]-hept-5-ene-2-carboxaldehyde (0.1 mole) was slowly added at room temperature, and the mixture was reacted at the same temperature for 10 hours. After the reaction was completed, the procedure of Example 28 was repeated to obtain the compound of Chemical Formula 34 as a colorless and clear liquid (23 g/yield: 90%).

<Chemical Formula 34>

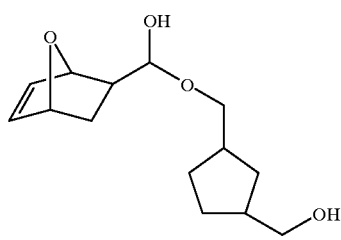

EXAMPLE 33

Synthesis of oxabicyclo[2.2.1]hept-5-ene-2-[(2-hydroxymethyl cyclopentyl)methoxy]methanol To a solution of sodium hydride (0.1 mole) in 100 ml of 1,2-cyclopentanedimethanol, oxabicyclo[2.2.1]-hept-5-ene-2-carboxaldehyde (0.1 mole) was slowly added at room temperature, and the mixture was reacted at the same temperature for 10 hours. After the reaction was completed, the procedure of Example 28 was repeated to obtain the compound represented by following Chemical Formula 35 as a colorless and clear liquid (23 g/yield: 90%).

<Chemical Formula 35>

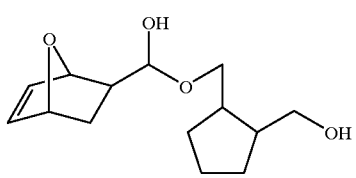

EXAMPLE 34

Synthesis of oxabicyclo[2.2.1]hept-5-ene-2-(3-hydroxycyclopentyloxy)methanol

To a solution of sodium hydride (0.1 mole) in 100 ml of 1,3-cyclopentanediol, oxabicyclo[2.2.1]-hept-5-ene-2-carboxaldehyde (0.1 mole) was slowly added at room temperature, and the mixture was reacted at the same temperature for 10 hours. After the reaction was completed, the procedure of Example 28 was repeated to obtain the compound represented by following Chemical Formula 36 as a colorless and clear liquid (20 g/yield: 87%).

<Chemical Formula 36>

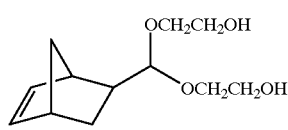

EXAMPLE 35

Synthesis of oxabicyclo[2.2.1]hept-5-ene-2-(2-hydroxycyclopentyloxy)methanol

To a solution of sodium hydride (0.1 mole) in 100 ml of 1,2-cyclopentanediol, oxabicyclo[2.2.1]-hept-5-ene-2-carboxaldehyde (0.1 mole) was slowly added at room temperature, and the mixture was reacted at the same temperature for 10 hours. After the reaction was completed, the procedure of Example 28 was repeated to obtain the compound represented by following Chemical Formula 37 as a colorless and clear liquid (20.4 g/yield: 85%).

<Chemical Formula 37>

EXAMPLE 36

Synthesis of 5-norbornene-2-di(2-hydroxyethoxy)methane

The procedure of Example 4 was repeated but using twice as many moles of ethylene glycol to obtain the compound represented by the following Chemical Formula 38 as a colorless and clear liquid.

<Chemical Formula 38>

EXAMPLE 37

Synthesis of 5-norbornene-2-di(3-hydroxypropoxy)methane

The procedure of Example 5 was repeated but using twice as many moles of trimethylene glycol to obtain the compound represented by following Chemical Formula 39 as a colorless and clear liquid.

<Chemical Formula 39>

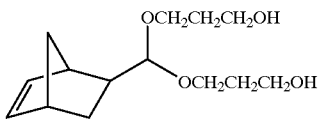

EXAMPLE 38

Synthesis of 5-norbornene-2-di(4-hydroxybutoxy)methane

The procedure of Example 6 was repeated but using twice as many moles of 1,4-butanediol to obtain the compound represented by following Chemical Formula 40 as a colorless and clear liquid.

<Chemical Formula 40>

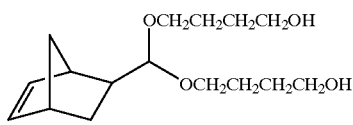

EXAMPLE 39

Synthesis of 5-norbornene-2-di(5-hydroxypentoxy)methane

The procedure of Example 7 was repeated but using twice as many moles of 1,5-pentanediol to obtain the compound represented by following Chemical Formula 41 as a colorless and clear liquid.

<Chemical Formula 41>

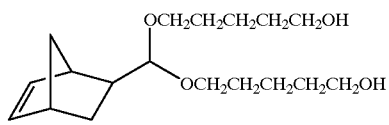

EXAMPLE 40

Synthesis of 5-norbornene-2-di[2-(2'-hydroxyethoxy)ethoxy]methane

The procedure of Example 8 was repeated but using twice as many moles of diethylene glycol to obtain the compound represented by following Chemical Formula 42 as a colorless and clear liquid.

<Chemical Formula 42>

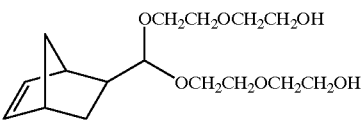

EXAMPLE 41

Synthesis of 5-norbornene-2-di{2-[2'-(2''-hydroxyethoxy)ethoxy]ethoxy} methane

The procedure of Example 9 was repeated but using twice as many moles of triethylene glycol to obtain the compound represented by following Chemical Formula 43 as a colorless and clear liquid.

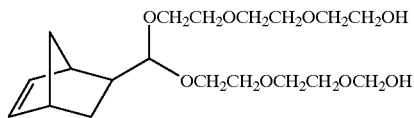
<Chemical Formula 43>

EXAMPLE 42

Synthesis of oxabicyclo[2.2.1]hept-5-ene-2-di(2-hydroxyethoxy) methane

The procedure of Example 22 was repeated but using twice as many moles of ethylene glycol to obtain the compound represented by following Chemical Formula 44 as a colorless and clear liquid.

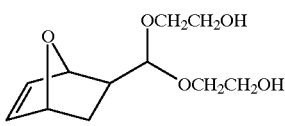
<Chemical Formula 45>

EXAMPLE 43

Synthesis of oxabicyclo[2.2.1]hept-5-ene-2-di(3-hydroxypropoxy) methane

The procedure of Example 23 was repeated but using twice as many moles of trimethylene glycol to obtain the compound represented by following Chemical Formula 45 as a colorless and clear liquid.

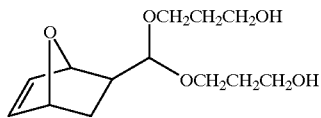
<Chemical Formula 45>

EXAMPLE 44

Synthesis of oxabicyclo[2.2.1]hept-5-ene-2-di(4-hydroxybutoxy) methane

The procedure of Example 24 was repeated but using twice as many moles of 1,4-butanediol to obtain the compound represented by following Chemical Formula 46 as a colorless and clear liquid.

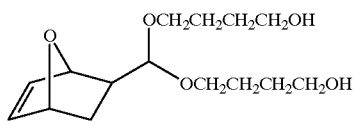
<Chemical Formula 46>

EXAMPLE 45

Synthesis of oxabicyclo [2.2.1]hept-5-ene-2-di(5-hydroxypentoxy) methane

The procedure of Example 25 was repeated but using twice as many moles of 1,5-pentanediol to obtain the compound represented by following Chemical Formula 47 as a colorless and clear liquid.

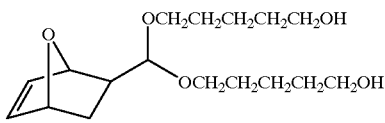
<Chemical Formula 47>

EXAMPLE 46

Synthesis of oxabicyclo[2.2.1]hept-5-ene-2-di[2-(2'-hydroxyethoxy)ethoxy] methane The procedure of Example 26 was repeated but using twice as many moles of diethylene glycol to obtain the compound represented by following Chemical Formula 48 as a colorless and clear liquid.

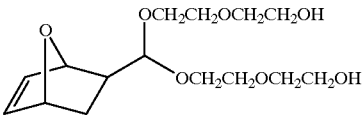
<Chemical Formula 48>

EXAMPLE 47

Synthesis of oxabicyclo[2.2.1]hept-5-ene-2-di {2-[2'-(2"-hydroxyethoxy)ethoxy]ethoxy} methane The procedure of Example 27 was repeated but using twice as many moles of triethylene glycol to obtain the compound represented by following Chemical Formula 49 as a colorless and clear liquid.

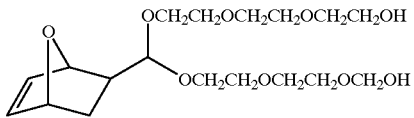
<Chemical Formula 49>

What is claimed is:

1. A compound represented by following Chemical Formula 1:

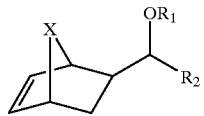

wherein, X represents $CH_2$, $CH_2CH_2$, or oxygen;

$R_1$ represents hydrogen, $C_1$–$C_5$ alkyl, or R'OH;

$R_2$ represents —OH, $C_1$–$C_5$ alkoxy, or —OR'—OH;

R' represents:

—$(CH_2)_{\overline{m}}$—,   —$(CH_2CH_2O)_nCH_2CH_2$—,   or

-continued

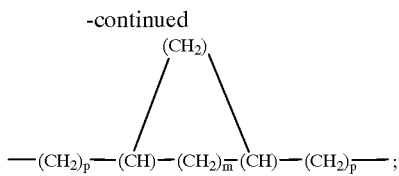

and m is an integer from 1–5, n is 1 or 2 and p is 0 or 1.

2. A compound according to claim 1, which is selected from the group consisting of:

5-norbornene-2-(1-methoxy)methanol,
5-norbornene-2-(1-ethoxy)methanol,
5-norbornene-2-(1-propyloxy)methanol,
5-norbornene-2-hydroxyethoxy methanol,
5-norbornene-2-hydroxypropyloxy methanol,
5-norbornene-2-hydroxybutyloxy methanol,
5-norbornene-2-hydroxypentyloxy methanol,
5-norbornene-2-hydroxyethoxyethoxy methanol,
5-norbornene-2-hydroxyethoxyethoxyethoxy methanol,
5-norbornene-2-(4-hydroxymethyl)cyclohexylmethoxy methanol,
5-norbornene-2-(3-hydroxymethyl)cyclohexylmethoxy methanol,
5-norbornene-2-(3-hydroxy)cyclohexyloxy methanol,
5-norbornene-2-(4-hydroxy)cyclohexyloxy methanol,
5-norbornene-2-(3-hydroxymethyl)cyclopentylmethoxy methanol,
5-norbornene-2-(2-hydroxymethyl)cyclopentylmethoxy methanol,
5-norbornene-2-(3-hydroxy)cyclopentyloxy methanol,
5-norbornene-2-(2-hydroxy)cyclopentyloxy methanol,
oxabicyclo[2.2.1]hept-5-ene-2-di(3-hydroxypropoxy) methane,
oxabicyclo[2.2.1]hept-5-ene-2-di(4-hydroxybutoxy) methane,
oxabicyclo[2.2.1]hept-5-ene-2-di(5-hydroxypentoxy) methane,
oxabicyclo[2.2.1]hept-5-ene-2-di[2-(2'-hydroxyethoxy)ethoxy] methane and
oxabicyclo[2.2.1]hept-5-ene-2-di{2-[2'-(2''-hydroxyethoxy)ethoxy]ethoxy} methane.

3. A compound according to claim 1, wherein each —OR'OH is independently selected from the group consisting of:

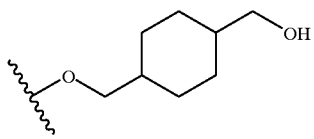

2

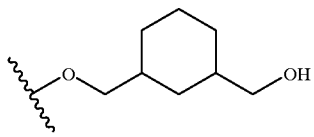

3

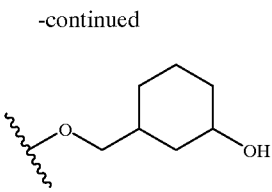

4

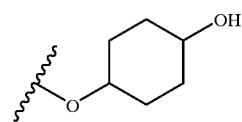

5

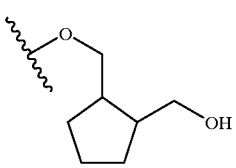

6

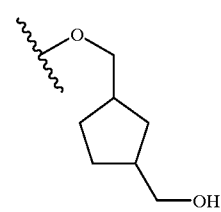

7

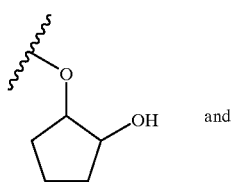

8 and

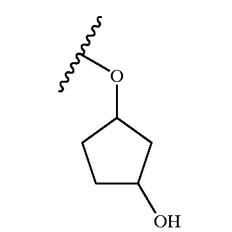

9

4. A process for preparing a compound of Chemical Formula 1:

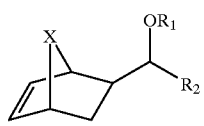

wherein, X represents $CH_2$, $CH_2CH_2$, or oxygen;

$R_1$ represents hydrogen, $C_1$–$C_5$ alkyl, or R'OH;

$R_2$ represents —OH, $C_1$–$C_5$ alkoxy, or —OR'—OH;

R' represents:

—$(CH_2)_{\overline{m}}$—, —$(CH_2CH_2O)_nCH_2CH_2$—, or

-continued

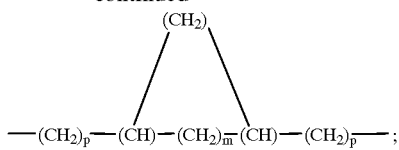

and
m is an integer from 1–5, n is 1 or 2 and p is 0 or 1;
which comprises reacting (i) a compound represented by Chemical Formula 2:

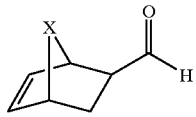

wherein X represents $CH_2$, $CH_2CH_2$, or oxygen,
with (ii) an alkyl compound having one or more hydroxyl substituents, in the presence of a base or acid catalyst.

5. A process according to claim 4, wherein the alkyl compound having hydroxyl group(s) is selected from the group consisting of methanol, ethanol, propanol, ethylene glycol, trimethylene glycol, 1,4-butanediol, 1,5-pentanediol, diethylene glycol, triethylene glycol, 1,4-cyclohexanedimethanol, 1,3-cyclohexanedimethanol, 1,3-cyclohexanediol, 1,4-cyclohexanediol, 1,3-cyclopentanedimethanol, 1,2-cyclopentanedimethanol, 1,3-cyclopentanediol and 1,2-cyclopentanediol.

6. A process according to claim 4, wherein the acid catalyst is selected from the group consisting of sulfuric acid, hydrochloric acid, nitric acid and acetic acid.

7. A process according to claim 4, wherein the base catalyst is selected from the group consisting of sodium hydride, potassium hydride, calcium hydride and lithium diisopropyl amide.

8. A process according to claim 4, wherein the reaction solvent is selected from the group consisting of tetrahydrofuran, dimethylformamide, dimethylsulfoxide, dioxane, benzene, toluene, and xylene.

* * * * *

UNITED STATES PATENT AND TRADEMARK OFFICE
CERTIFICATE OF CORRECTION

PATENT NO. : 6,359,153 B1
DATED : March 19, 2002
INVENTOR(S) : Geun Su Lee et al.

It is certified that error appears in the above-identified patent and that said Letters Patent is hereby corrected as shown below:

Column 7,
Line 29, the phrase "(21 g/yield: 88)%." should read -- (21 g/yield: 88%). --.
Line 65, the term "cyclopentylnethoxy" should read -- cyclopentylmethoxy --.

Column 10,
Line 46, please insert a left bracket after the term "oxabicyclo".

Column 11,
Line 6, the term "<Chemical Formula 19>" should read -- <Chemical Formula 25> --.
Line 18, please insert a right parenthesis after the term -- "hydroxybutoxy" --.

Column 12,
Lines 12-13, the term "hept-5-ene-2-{2-[2-(2'2"-hydroxyethoxy" should read
-- hept-5-ene-2-{2-[2'-(2"-hydroxyethoxy --.
Lines 50-57, please replace Chemical Formula 30 with the following formula:
--

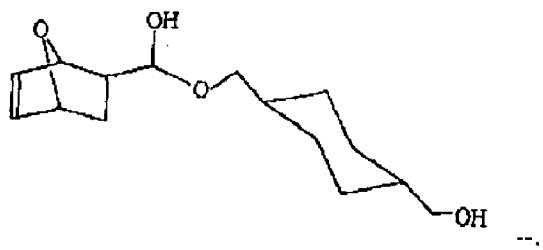

--.

Line 61, please insert a right bracket between the terms "methoxyl" and "methanol".

Column 13,
Line 52, please insert a left bracket after the term "oxabicyclo".

Column 17,
Line 22, the term "Chemical Formula 45" should read -- Chemcial Formula 44 --.

UNITED STATES PATENT AND TRADEMARK OFFICE
CERTIFICATE OF CORRECTION

PATENT NO.   : 6,359,153 B1
DATED        : March 19, 2002
INVENTOR(S)  : Geun Su Lee et al.

It is certified that error appears in the above-identified patent and that said Letters Patent is hereby corrected as shown below:

Column 19,
Between lines 38-39, please insert the following:

```
--oxabicyclo[2.2.1]hept-5-ene-2-methanol,
oxabicyclo[2.2.1]hept-5-ene-2-(1-methoxy)methanol,
oxabicyclo[2.2.1]hept-5-ene-2-(1-ethoxy)methanol,
oxabicyclo[2.2.1]hept-5-ene-2-(1-propoxy)methanol,
oxabicyclo[2.2.1]hept-5-ene-2- (2-hydroxyethoxy)methanol,
oxabicyclo[2.2.1]hept-5-ene-2- (3-hydroxypropoxy)methanol,
oxabicyclo[2.2.1]hept-5-ene-2- (4-hydroxybutoxy)methanol,
oxabicyclo[2.2.1]hept-5-ene-2- (5-hydroxypentoxy)methanol,
oxabicyclo[2.2.1]hept-5-ene-2- [2-(2'-hydroxyethoxy)ethoxy]methanol,
oxabicyclo[2.2.1]hept-5-ene-2- {2-[2'-(2"-hydroxyethoxy)ethoxy]ethoxy}methanol,
oxabicyclo[2.2.1]hept-5-ene-2- [(4-hydroxymethyl cyclohexyl)methoxy]methanol,
oxabicyclo[2.2.1]hept-5-ene-2- [(3-hydroxymethyl cyclohexyl)methoxy]methanol,
oxabicyclo[2.2.1]hept-5-ene-2- (3-hydroxycyclohexyloxy)methanol,
oxabicyclo[2.2.1]hept-5-ene-2- (4-hydroxycyclohexyloxy)methanol,
oxabicyclo[2.2.1]hept-5-ene-2- [(3-hydroxymethyl cyclopentyl)methoxy]methanol,
oxabicyclo[2.2.1]hept-5-ene-2- [(2-hydroxymethyl cyclopentyl)methoxy]methanol,
oxabicyclo[2.2.1]hept-5-ene-2- (3-hydroxycyclopentyloxy)methanol,
oxabicyclo[2.2.1]hept-5-ene-2- (2-hydroxycyclopentyloxy)methanol,
5-norbornene-2 -di(2-hydroxyethoxy) methane,
5-norbornene-2 -di(3-hydroxypropoxy) methane,
5-norbornene-2 -di(4-hydroxybutoxy) methane,
5-norbornene-2 -di(5-hydroxypentoxy) methane,
5-norbornene-2-di[2-(2'-hydroxyethoxy)ethoxy] methane,
5-norbornene-2 -di{2-[2'-(2"-hydroxyethoxy)ethoxy]ethoxy} methane,
oxabicyclo[2.2.1]hept-5-ene-2 -di(2-hydroxyethoxy) methane,--.
```

Column 20,
Lines 3-8, please replace the chemical structure with the following:
--

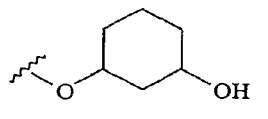

--.

Signed and Sealed this

First Day of April, 2003

JAMES E. ROGAN
*Director of the United States Patent and Trademark Office*